(12) United States Patent
Lorenzon

(10) Patent No.: US 9,034,385 B2
(45) Date of Patent: May 19, 2015

(54) PRODUCT BASED ON CONJUGATED LINOLEIC ACID AND A METHOD FOR THE MANUFACTURE THEREOF

(75) Inventor: Maurizio Lorenzon, Noale (IT)

(73) Assignee: SILA S.R.L., Noale (VE) (IT)

( * ) Notice: Subject to any disclaimer, the term of this patent is extended or adjusted under 35 U.S.C. 154(b) by 607 days.

(21) Appl. No.: 12/527,033

(22) PCT Filed: Jan. 11, 2008

(86) PCT No.: PCT/EP2008/050281
§ 371 (c)(1),
(2), (4) Date: Aug. 13, 2009

(87) PCT Pub. No.: WO2008/098807
PCT Pub. Date: Aug. 21, 2008

(65) Prior Publication Data
US 2010/0092569 A1    Apr. 15, 2010

(30) Foreign Application Priority Data

Feb. 14, 2007   (IT) .............................. PD2007A0049

(51) Int. Cl.
| | | |
|---|---|---|
| *A61K 9/14* | (2006.01) | |
| *A23K 1/18* | (2006.01) | |
| *A23D 9/05* | (2006.01) | |
| *A23K 1/00* | (2006.01) | |
| *A23K 1/16* | (2006.01) | |
| *A23L 1/00* | (2006.01) | |
| *A23L 1/30* | (2006.01) | |

(52) U.S. Cl.
CPC ........... *A23K 1/1813* (2013.01); *A23C 2230/10* (2013.01); *A23D 9/05* (2013.01); *A23K 1/002* (2013.01); *A23K 1/004* (2013.01); *A23K 1/005* (2013.01); *A23K 1/164* (2013.01); *A23K 1/1643* (2013.01); *A23L 1/0032* (2013.01); *A23L 1/3008* (2013.01); *A23V 2002/00* (2013.01)

(58) Field of Classification Search
CPC . A23C 2230/10; A23D 9/05; A23V 2002/00; A23V 2200/30; A23V 2250/1866; A23V 2250/1942; A23V 2200/224; A23L 1/3008; A23L 1/0032; A23K 1/1813; A23K 1/1643; A23K 1/164; A23K 1/005; A23K 1/002; A23K 1/004
USPC ........................................... 424/490; 514/560
See application file for complete search history.

(56) References Cited

U.S. PATENT DOCUMENTS

| | | | |
|---|---|---|---|
| 4,755,387 A * | 7/1988 | Tzeghai et al. ................ | 424/450 |
| 2002/0081315 A1* | 6/2002 | Katz et al. ................ | 424/195.16 |
| 2005/0208195 A1* | 9/2005 | Mizusawa et al. ............ | 426/601 |
| 2006/0068019 A1* | 3/2006 | Dalziel et al. ................. | 424/490 |
| 2006/0073205 A1* | 4/2006 | Ohta et al. .................... | 424/471 |

FOREIGN PATENT DOCUMENTS

| | | | | |
|---|---|---|---|---|
| WO | 92/21249 A1 | 12/1992 | | |
| WO | 01/56545 A2 | 8/2001 | | |
| WO | 03/045168 A1 | 6/2003 | | |
| WO | 03/059088 A1 | 7/2003 | | |
| WO | WO03/059088 | * | 7/2003 | ............... A23K 1/18 |
| WO | 2004/080199 A2 | 9/2004 | | |

OTHER PUBLICATIONS

Veerawat Teeranachaideekul, et al, Encapsulation of Ascorbyl Palmitate in Nanostructured Lipid carriers (NLC)—Effects of Formulation Parameters on Physicochemical Stability, 340 Int'l. J Pharma. 198 (2007).*
Volkhard Jenning & Sven Gohla, Comparison of Wax and Glyceride Solid Lipid Nanoparticles (SLN), 196 Int'l. J Pharma. 219 (2000).*
International Search Report and Written Opinion from PCT Application PCT/EP2008/050281 mailed May 6, 2008.
Perfield et al., "Effects of amide-protected and lipid-encapsulated conjugated linoleic acid (CLA) supplements on milk fat synthesis," J. of Dairy Science, vol. 87, No. 9, Sep. 2004, pp. 3010-3016 (XP002449597).

* cited by examiner

*Primary Examiner* — Sean Basquill
(74) *Attorney, Agent, or Firm* — Kristina Castellano; Castellano PLLC

(57) ABSTRACT

A product based on conjugated linoleic acid (CLA) comprises an inner core in which the conjugated linoleic acid is substantially concentrated as well as a coating for covering and protecting the inner core; the coating in turn comprises a fraction greater than 80% by weight relative to the coating of a lipid matrix formed by glycerides of C16, C18, C20 and C22 saturated fatty acids.

25 Claims, No Drawings

PRODUCT BASED ON CONJUGATED LINOLEIC ACID AND A METHOD FOR THE MANUFACTURE THEREOF

CLAIM FOR PRIORITY

The present application is a U.S. National Stage Application of PCT/EP2008/050281 filed on Jan. 11, 2008, which claims priority to Italian application PD2007A000049 filed Feb. 14, 2007, the contents of both of which are incorporated herein by reference.

FIELD

The present invention relates to a product based on conjugated linoleic acid (hereinafter abbreviated to CLA) or derivatives thereof having the characteristics set out in the preamble to the main claim. The invention is also directed towards a method for the manufacture of the product.

BACKGROUND ART

The collective term CLA is intended to describe a mixture of geometric and positional, conjugated, dienoic isomers derived from linoleic acid, both in the form of free fatty acids (FFAs) and in the form of the respective salts or other derivatives, particularly esters.

CLA is present in nature in the milk and meat of ruminants and is formed as an intermediate compound during the process of biohydrogenation of some polyunsaturated fatty acids contained in their diet, in particular of linoleic acid and of α-linolenic acid. Some of these intermediate compounds escape complete hydrogenation and accumulate in the mammary glands.

The CLA isomer which is predominant in the fatty fraction of ruminant milk is cis-9,trans-11 for which an endogenous synthesis mechanism has also been proposed (Mahfouz et al., 1980, Pollard et al., 1980, Griinari et al., 2000).

Studies carried out within the last three decades have shown this isomer, together with the trans-10,cis-12 isomer, to be involved in many physiological and metabolic functions; this has progressively increased scientific interest in CLA and the biochemical mechanisms in which it is involved.

In particular, the following are indicated, amongst the numerous potential applications of CLA: i) inhibition of carcinogenesis; ii) improvement in immune function; iii) reduction in inflammation; iv) reduction in the catabolic effects of immune stimulation; v) reduction in asthma in animal models; vi) reduction in atherosclerosis (reduction in the LDL (low density lipoprotein) concentration and in the LDL:HDL (high density lipoprotein) ratio); vii) reduction in accumulation of body fat and increase in lean body mass; viii) increased growth in rodent young; ix) reduction in diabetes symptoms in some experimental models; x) reduction in hypertension.

Not all of the physiological effects given above can be attributed to both of the above-mentioned isomers (as is, however, true for the inhibition of mammary carcinogenesis); in some cases, the effect is determined by only one of the two (for example, trans-10,cis-12 is the only isomer which is responsible for reducing body fat mass, whilst the isomer cis-9,trans-11 improves growth and feeding efficiency in rodent young) whereas, in other cases, the effect of the two isomers seems to be a balancing of opposing actions.

In the light of the above-described potential beneficial effects, a need has arisen to increase the availability of CLA both by trying to produce, from ruminants, milk which is richer in that compound, and by trying to provide a CLA-based product for direct administration to human beings, for example, in the form of a food supplement or additive for use in normal food production. In the first case, one of the possible alternatives provides for the supplementing of the animal diet with synthetically produced CLA.

It is also known to synthesize CLA in the laboratory, for example, from vegetable oils such as safflower oil or sunflower oil; the product which is generally obtained is a mixture of isomers of CLA in its various forms such as methyl esters or free fatty acids (FFAs) and can be used in both human and animal food. However, CLA has great disadvantages in terms of stability.

In fact it tends to react very easily with oxygen and other oxidizing agents such as choline hydrochloride or some minerals, particularly in the presence of light or of metals such as copper and iron, degrading rapidly and thus losing its activity. Its poor resistance to oxidation processes renders it particularly unstable and much less easily handled than normal polyunsaturated fatty acids.

CLA must therefore be suitably protected both from the outside environment (during the periods, possibly quite long periods, which elapse between its production and its use) and from the gastric or pre-gastric environment (during use).

Moreover, the high degree of instability of CLA also imposes considerable limitations on the manufacturing processes which lead to its protection; in fact processes in which high temperatures are required for fairly long periods of time would lead to its rapid degradation.

Currently known methods of protecting CLA provide for the use of CLA in the form of calcium salts or in the form of esters, or for the encapsulation of the molecule in a matrix of casein treated with formaldehyde, or even microencapsulation in cyclodextrin.

However, the goal of providing CLA with the characteristics of stability required by the market has not yet been achieved. There is therefore still a need in the sector to have available a CLA-based product the CLA content and, in particular, the resistance to oxidation of which remains substantially unchanged, even over a long period of time of the order of several years, without the need to resort to the use of antioxidants or to storage in an inert atmosphere and which, at the same time, can also remain stable in the gastrointestinal tracts of animals and human beings.

DESCRIPTION

The problem underlying the present invention is that of providing a CLA-based product, as well as a method for the manufacture thereof, which are designed structurally and functionally to overcome the limitations discussed above with reference to the prior art mentioned.

This problem is solved by the present invention by means of a product and a method according to the appended claims.

The product produced in accordance with the present invention is of the encapsulated type and comprises an inner core in which the CLA is substantially concentrated, and a coating completely surrounding the inner core to cover and protect it.

The final product may have any suitable shape or size but is preferably produced in granular form with dimensions of between 0.15 and 2 millimeters, wherein at least 80% of the product has a particle size of less than 0.8 mm.

The granular product is advantageously produced by a microencapsulation process by means of a spray cooling technique which is described in detail below.

The CLA used is preferably of synthetic derivation in free fatty acid and/or methyl ester form. It is in the form of an oily liquid in which the content of the two principal isomers of CLA, cis-9,trans-11 and trans-10,cis-12, is as high as possible, preferably at least 50% by weight. The two isomers are normally present in almost equivalent quantities.

The content of the two principal isomers of CLA that are present in the CLA synthesis oil will be referred to below by the term "CLA content".

The CLA content may be variable according to the raw material used for its production (sunflower or safflower oil) and may be, for example, 60% or 80% for use both in animal feed and in human food.

The CLA used for the production of the product according to the invention has a peroxide number (measured in accordance with Italian standard NGD C 35-1976) which is as low as possible, preferably less than 10 and even more preferably less than 3.

The peroxide number of CLA is a parameter that is indicative of the degradation of the CLA; the higher the peroxide number is, the greater is the degree of degradation of the CLA.

It has been found that a sufficiently low peroxide number in the CLA that is used as the raw material of the product according to the invention enables the product to keep its characteristics unchanged for a long time, whereas a raw material which is already highly oxidized continues in its degradation process even though at very slow rates, in spite of the lipid matrix coating.

Similarly, the CLA used as raw material must be negative to the Kreis test (Italian standard NGD C 56-1979) for the identification of any aldehydes resulting from the CLA degradation process, and must show as low as possible a p-anisidine number.

In a first step of the method for the manufacture of the product of the invention, the CLA, which is liquid at ambient temperature, is completely adsorbed on a solid substrate. The latter is preferably inorganic so as to withstand degradation phenomena for a longer period of time.

To reduce as far as possible the time required for the completion of this step, it is carried out at a temperature of about 60-70° C. in a high-speed stirrer. In these conditions a few minutes normally suffice to achieve the desired effect.

In particular, the preferred solid substrate is silica-based and is in powder form with mean dimensions of between 10 and 80 microns, preferably between 15 and 20 microns.

The silica used is preferably of synthetic derivation and substantially free of metals so as to avoid the triggering of oxidative processes and possible contamination of the CLA.

It is important to stress that, as well as adsorbing the CLA, the silica confers a suitable consistency on the mixture which is produced in a subsequent processing step for admission to the spray cooling chamber so as to promote the correct formation of the finished granular product.

Again for the purposes of regulating the consistency of the mixture to be admitted to the spray chamber, other mineral agents such as, for example, calcium carbonate or calcium sulphate dihydrate may also optionally be used in addition to the silica.

The quantity of silica used will be that which is sufficient to achieve complete adsorption of the CLA, generally between 33% and 55% relative to the CLA.

Upon completion of this first step of the method, a free-flowing, powdery material is obtained, which will constitute the inner core of the finished product.

In a second method step immediately following the first, the powdery material obtained is mixed with a lipid matrix which will form the coating for covering and protecting the inner core.

According to a first aspect of the invention, the lipid matrix comprises, for at least 80% of its weight, glycerides of saturated fatty acids with 16, 18, 20 and 22 carbon atoms (briefly C16, C18, C20 and C22).

The term "saturated" should not be understood in the absolute sense but is intended to indicate fatty acids having a degree of saturation of at least 99%.

As shown by tests carried out by the Applicant and reported below, it is particularly important that the fatty acids which are present in the matrix be present substantially in the form of glycerides and not free acids. For this purpose, the percentage of free acids within the lipid matrix must be less than 10% and preferably less than 1%.

The glycerides are preferably in the form of triglycerides.

The lipid matrix according to the invention preferably also has a C18 saturated fatty acid content greater than 85% relative to the total saturated fatty acids constituting the glycerides.

This characteristic wholly unexpectedly gives the lipid matrix, and hence the coating, a protective effect with respect to CLA which is much greater than that of matrices in which other fatty acids amongst those mentioned above are preponderant.

The lipid matrix is such as to have a melting point of between 60° C. and 75° C., preferably between 65° C. and 68° C.

The lipid matrix is first melted and then mixed with the powdery material obtained by the adsorption of the CLA on the silica. The mixing may optionally take place in the presence of suitable emulsifiers so as to promote a homogeneous dispersion of the silica powder in the lipid matrix.

The ratio between lipid matrix (triglycerides+emulsifiers) and CLA depends on the type of product (in particular on the size) to be obtained. In the preferred embodiment described herein, the ratio is generally between 1.3 and 1.5, preferably 1.4.

The mixing is carried out for a period of about 5-20 minutes, preferably about 10 minutes, to give a homogeneous mixture (although, more precisely, the system obtained can better be defined as a homogeneous suspension of a solid powder in a lipid matrix).

The mixture is then immediately injected at high pressure by means of nozzles of suitable shape into a cold spraying chamber in which the temperature is kept between −2° C. and −12° C. so that, during the short time for which the mixture particles remain in air, the lipid matrix can advantageously solidify in accordance with known procedures (spray cooling technique).

A solid, granular product comprising an inner core formed by the solid substrate particles in which the CLA is adsorbed and a coating, formed by the lipid matrix, for covering and protecting the inner core is thus obtained.

After spraying, the product is collected on conveyor belts and, whilst still inside the cold chamber, is subjected to forced ventilation so as to leave the chamber at a temperature below 25° C.

To prevent agglutination of the granular product, it is sprinkled with an anti-agglutination agent constituted, for example, by silica with a particle size of between 75 and 80 microns, in a proportion of about 0.5-2% relative to the product.

The granule size depends on the supply pressure and on the nozzle shape but, if necessary, the product can be screened to make it conform to the desired size specifications.

By virtue of the specific method of production and of the matrix used, the coating obtained is arranged continuously and uniformly around the inner core of conjugated linoleic acid adsorbed on silica. This prevents the exposure of the CLA to environmental oxygen, to light, and to the oxidizing substances that are present in preparations for human and/or animal use during the storage period prior to its use. Moreover, it prevents or reduces microbial biohydrogenation which may take place in the rumen when used in the feeding of ruminants. The product thus microencapsulated can be used, according to the dosage, both in the production of drugs and in the production of food supplements which in turn are intended for both human and animal food.

Another important advantage achieved by the method according to the present invention is that the period of time for which the CLA is exposed to the atmosphere is very limited, of the order of 20 minutes. This permits operation in a normal atmosphere.

EXAMPLES OF THE PRODUCTION OF THE PRODUCT ACCORDING TO THE INVENTION

Example 1

34 g of CLA oil (with a content of 60%) was introduced into a mixer with a jacket, heated to a temperature of 70° C., and was adsorbed by 14.4 g of silica to which 5 g of calcium carbonate was added, to give a free-running, powdery material.

A lipid matrix constituted by 43.4 g of triglycerides of C16, C18, C20 and C22 saturated fatty acids, in which the C18 content was 85%, and by 3 g of emulsifiers, brought to a temperature of 70° C., was added to the powdery material and stirred for about 10 minutes to give a homogeneous suspension.

The mixture thus obtained was then supplied to a cold chamber kept at a temperature of about −10° into which it was sprayed with the use of a nozzle suitable for the desired particle size so as to give granules with an inner core based on CLA adsorbed on silica and coated with a lipid matrix.

About 0.9 g of silica was dispersed on the microcapsules extracted from the cold chamber and the whole was subjected to screening to define the dimensions of the finished product (80% less than 800 microns).

Example 2

A second sample of product was produced by the same method as in the preceding example, with the difference that the triglycerides comprised a quantity of about 45% of C18 saturated fatty acid and a quantity of about 60% of C16 saturated fatty acid.

Example 3

Comparative

A third sample of product was produced by the same method as in Example 1 with the difference that the matrix used was formed by free, long-chain, saturated fatty acids with a stearic acid (C18) content of 98%.

Analysis of the Products

The samples produced above were subjected to a first series of laboratory tests directed towards determining their stability over time with respect to environmental factors and to different oxidants. In particular, the various samples were packaged in paper bags with aluminium foil and internal PE and stored in a store.

Stability was assessed by measuring, over time, the CLA content and the peroxide number which, as stated above, constitutes an index of the degree of degradation of the CLA and of the lipid matrix.

A preliminary test consisted in assessing the stability over time of the CLA adsorbed in silica but without the lipid matrix coating. The sample was kept in the dark for one week, at the end of which a 35% reduction of the CLA content from 19.8% to 12.9% was noted. This test shows that the presence of the coating is necessary for the stability of the CLA.

The tests showed that the sample of Example 3, in which the matrix was formed substantially by C18 fatty acid rather than by triglycerides, was decidedly less stable over time. In fact it started to lose its initial content only a few days after production; after three months the CLA concentration was zero (initial content 20.35%; content after keeping for three months: 0%) and, at the same time, an increase in the peroxide number from 3.2 to 50 was observed.

The product also showed a marked tendency to agglutinate by means of an exothermic chemical reaction between the CLA and the matrix.

A slightly improved performance in terms of stability was noted with the sample of Example 2 which, after storage for six months, showed an approximately 84% loss of CLA content, which went from the initial 19.98% to 3.19%. Moreover, the CLA tended to escape from the microcapsules through the coating.

Wholly surprisingly, Sample 1, on the other hand, showed excellent stability throughout the measurement period. In fact, after as long as two years, the reduction in CLA content measured was only 6%, from 20.0% to 18.8%.

A second series of tests was performed in vivo on milking cows to check the efficacy of the protection of the CLA in the gastrointestinal tracts of ruminants.

The test was carried out with the use of samples of CLA-based product obtained in accordance with Example 1 and in accordance with Example 3, administered to distinct groups of milking cows in various doses for a period of one month.

The milk obtained from each group of animals upon completion of the treatment was then analyzed to measure its CLA methyl ester content, also comparing it with a sample of milk taken from a group of cows that were not treated and with a sample of commercially-available, packaged milk.

The various milk samples were then further analyzed to identify their acid profiles by measuring the respective fractions of saturated fatty acids, of monounsaturated fatty acids, and of polyunsaturated fatty acids.

The type of sample administered for each group of animals, the doses administered, as well as the results obtained by the analysis of the milk samples are summarized in Table 1 below.

TABLE 1

| Group | 1 | 2 | 3 | 4 | 5* |
|---|---|---|---|---|---|
| Dose of product (g/head/day) | 20 | 50 | 50 | 0 | — |
| Type of product | Ex. 1 | Ex. 1 | Ex. 3 | — | — |
| CLA (mg/kg milk) | 0.95 | 2.14 | 1.28 | 0 | 0 |
| % saturated fatty acids | 67.85 | 56.80 | 58.29 | 77.30 | 72.30 |
| % monounsaturated fatty acids | 30.07 | 39.54 | 39.24 | 20.65 | 25.20 |
| % polyunsaturated fatty acids | 2.09 | 3.67 | 2.47 | 2.05 | 2.07 |

*commercial milk sample

As can be seen from this table, CLA methyl ester was not present in the animals which had not been treated, which confirms that its presence is due to the administration of external CLA. It is clear from a comparison between Group 2 and Group 3 that the matrix based on triglycerides with 85% of C18 fatty acid was much more effective than the matrix composed of free C18 fatty acid in protecting the CLA from ruminal biohydrogenation processes and in rendering it thus available for absorption in the mammary glands.

Moreover, the comparison between Group 1 and Group 2 shows that the availability of the CLA was substantially proportional to the quantity of CLA administered, irrespective of the type of animal feeding.

A further important effect demonstrated by the above-described tests is that the administration to the cows of CLA according to the present invention advantageously modifies the acid profile of the milk obtained, drastically reducing the fraction of saturated fatty acids present in the milk in favour of the fraction of mono-unsaturated and poly-unsaturated fatty acids, with all of the positive consequences resulting therefrom.

The present invention thus solves the problem discussed above with reference to the prior art mentioned at the same time offering many further advantages.

The invention claimed is:

1. A product based on conjugated linoleic acid, comprising an inner core in which the conjugated linoleic acid (CLA) is substantially concentrated, and a coating for covering and protecting the inner core, wherein the coating comprises a lipid matrix comprising:
   a fraction greater than 80% by weight of glycerides of C16, C18, C20 and C22 saturated fatty acids, wherein the fraction of C18 fatty acid is equal or greater than 85% of the total fatty acids included in the lipid matrix and,
   wherein the glycerides comprise triglycerides having a free acidity less than 1%.

2. The product according to claim 1, wherein in the inner core, the CLA is adsorbed on a solid substrate in powdery form.

3. The product according to claim 2, wherein the solid substrate has a mean particle size of between 10 and 80 microns.

4. The product according to claim 2, wherein the solid substrate comprises silica substantially free of metals.

5. The product according to claim 4, wherein, in addition to the silica, the substrate comprises at least one mineral agent selected from the group consisting of calcium carbonate and calcium sulphate dihydrate.

6. The product according to claim 1, wherein the lipid matrix comprises an emulsifier.

7. The product according to claim 1, wherein the CLA is in the form of at least one of methyl ester, of free fatty acids, and of salts thereof, and comprises a fraction greater than 50% by weight of the cis-9,trans-11 and trans-10,cis-12 isomers.

8. The product according to claim 7, wherein the CLA comprises a fraction of about 60% by weight of the cis-9, trans-11 and trans-10,cis-12 isomers.

9. The product according to claim 7, wherein the CLA comprises a fraction of about 80% by weight of the cis-9, trans-11 and trans-10,cis-12 isomers.

10. The product according to claim 1, wherein the product is in granular form with a particle size of between 0.15 and 2 millimeters, and wherein at least 80% of the product has a particle size of less than 800 microns.

11. The product according to claim 10, wherein a ratio by weight between the lipid matrix and the CLA is between 1.3 and 1.5.

12. A method for the manufacture of a product based on conjugated linoleic acid (CLA) comprising coating an inner core in which the CLA is substantially concentrated with a coating, wherein the coating comprises a lipid matrix comprising:
   a fraction greater than 80% by weight of glycerides of C16, C18, C20 and C22 fatty acids, wherein the fraction of C18 fatty acid is equal or greater than 85% of the total fatty acids included in the lipid matrix and,
   wherein the glycerides comprise triglycerides having a free acidity less than 1%.

13. The method according to claim 12, wherein the CLA has a peroxide number of less than 10.

14. The method according to claim 12, wherein prior to being coated with the coating, the CLA is completely adsorbed on a solid substrate in powdery form so as to give a free-running, powdery material.

15. The method according to claim 14, wherein the solid substrate has a mean particle size of between 10 and 80 microns.

16. The method according to claim 14, wherein the solid substrate comprises silica substantially free of metals.

17. The method according to claim 14, wherein the adsorption is achieved by high-speed mixing.

18. The method according to claim 14, wherein the powdery material obtained by the adsorption of the CLA on the solid substrate is mixed with the lipid matrix at a temperature greater than the melting point of the matrix, the melting point being between 60° C. and 75° C., to give a mixture formed by a solid suspension in a molten lipid matrix.

19. The method according to claim 18, wherein the mixing between adsorbed CLA and lipid matrix is continued for a period of between 5 and 20 minutes.

20. The method according to claim 18, wherein the mixture is sprayed at high pressure through nozzles into a chamber which is kept at a temperature of between −2° C. and −12° C., so as to form a granular solid product.

21. The method according to claim 20, wherein a silica-based powder is dispersed onto the granular solid product as an anti-agglutination agent.

22. A food supplement for human consumption comprising the product based on conjugated linoleic acid (CLA) according to claim 1.

23. A feed supplement for animal consumption comprising the product based on conjugated linoleic acid (CLA) according to claim 1.

24. The product according to claim 5, wherein the solid substrate has a mean particle size of between 15 and 20 microns.

25. The method according to claim 14, wherein the solid substrate has a mean particle size of between 15 and 20 microns.

* * * * *